United States Patent
Kawabata et al.

(10) Patent No.: US 10,633,358 B2
(45) Date of Patent: Apr. 28, 2020

(54) T-TYPE CALCIUM CHANNEL INHIBITOR

(71) Applicants: KINKI UNIVERSITY, Higashiosaka-shi, Osaka (JP); FUSO PHARMACEUTICAL INDUSTRIES, LTD., Osaka-shi, Osaka (JP)

(72) Inventors: Atsufumi Kawabata, Higashiosaka (JP); Hideaki Matsuda, Higashiosaka (JP); Fumiko Sekiguchi, Higashiosaka (JP); Kazuya Murata, Higashiosaka (JP); Hiroyuki Nishikawa, Osaka (JP)

(73) Assignees: KINKI UNIVERSITY, Osaka (JP); FUSO PHARMACEUTICAL INDUSTRIES, LTD., Osaka (JP)

(*) Notice: Subject to any disclaimer, the term of this patent is extended or adjusted under 35 U.S.C. 154(b) by 14 days.

(21) Appl. No.: 15/807,064

(22) Filed: Nov. 8, 2017

(65) Prior Publication Data

US 2018/0065947 A1 Mar. 8, 2018

Related U.S. Application Data

(62) Division of application No. 14/892,392, filed as application No. PCT/JP2014/063102 on May 16, 2014, now abandoned.

(30) Foreign Application Priority Data

May 23, 2013 (JP) .................................. 2013-108512

(51) Int. Cl.
 *C07D 311/32* (2006.01)
 *A61K 31/352* (2006.01)

(52) U.S. Cl.
 CPC .......... *C07D 311/32* (2013.01); *A61K 31/352* (2013.01)

(58) Field of Classification Search
 CPC ............................ C07D 311/32; A61K 31/352
 See application file for complete search history.

(56) References Cited

U.S. PATENT DOCUMENTS

| | | | |
|---|---|---|---|
| 9,326,968 B2 * | 5/2016 | Rho ..................... | A61K 31/35 |
| 2003/0180394 A1 | 9/2003 | Erdelmeier et al. | |
| 2004/0137096 A1 | 7/2004 | Kuhrts | |
| 2005/0226943 A1 | 10/2005 | Yan et al. | |
| 2013/0303474 A1 | 11/2013 | Rho et al. | |

FOREIGN PATENT DOCUMENTS

| | | |
|---|---|---|
| EP | 1621201 A1 | 2/2006 |
| JP | 3327699 B2 | 7/2002 |
| JP | 4393062 B2 | 10/2009 |
| JP | 2010-195762 A | 9/2010 |
| JP | 2011140477 A | 7/2011 |
| KR | 2009-0010504 | 1/2009 |
| WO | 2011006073 A1 | 1/2011 |
| WO | 2011087755 A2 | 7/2011 |

(Continued)

OTHER PUBLICATIONS

NeuropathicPainPrevention, 2018, https://www.medicinenet.com/neuropathic_pain_nerve_pain/article.htm# can_neuropathic_pain_be_prevented.*
Cain et al., 2014, https://www.researchgate.net/publication/260437461_T-Type_ Calcium_Channels_and_Epilepsy.*
Hyperaldosteronism-2, 2018, https://medlineplus.gov/ency/article/000330.htm.*
Hyperaldosteronism, 2018, http://endocrinediseases.org/adrenal/hyperaldosteronism_treatment.shtml.*
T-type_calcium_channel_—_Wikipedia, 2018, https://en.wikipedia.org/wiki/T-type_calcium_channel.*
Santoni-et-al., British Journal of Pharmacology, 2012, 166, 1244-1246.*
Perez et al., Journal of Virology, 1999, vol. 73 No. 3, p. 2481-2490.*
Sawatdichaikul-et-al., J. Mol Model, 2012, 18, 1241-1254.*
Powell et al., British Journal of Clinical Pharmacology, 77 (5), 729-739, 2013.*

(Continued)

*Primary Examiner* — Sun Jae Yoo
(74) *Attorney, Agent, or Firm* — Hamre, Schumann, Mueller & Larson, P.C.

(57) ABSTRACT

The present invention provides a T-type calcium channel inhibitor which is a compound represented by formula (1), a pharmaceutically acceptable salt of this compound or a solvate of this compound. The present invention also provides: this T-type calcium channel inhibitor; a pharmaceutical product containing this T-type calcium channel inhibitor; and a therapeutic agent or prophylactic agent for diseases, the effective action of which is a T-type calcium channel inhibitory action. (In formula (1), each of $R^1$ and $R^2$ independently represents H, —OH or —$OR^{11}$ wherein $R^{11}$ represents a $C_{1-3}$ alkyl group; each of $R^3$ and $R^4$ independently represents H, —OH or —$OR^{12}$, wherein $R^{12}$ represents a $C_{1-3}$ alkyl group; and each of $R^5$ and $R^6$ independently represents H, a halogen atom, a $C_{1-10}$ alkyl group, a $C_{2-6}$ alkenyl group, a $C_{2-6}$ alkynyl group, a phenyl group (which may be substituted by a $C_{1-6}$ alkoxy group or a halogen atom), a —$C_{1-3}$ alkyl-phenyl group (which may be substituted by a $C_{1-6}$ alkyloxy group or a halogen atom) or a $C_{10-50}$ prenyl group.)

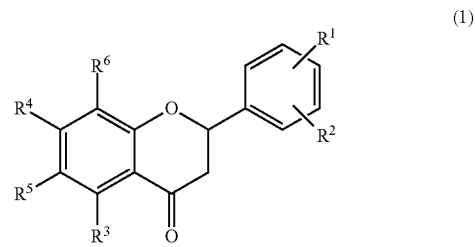

(1)

1 Claim, 10 Drawing Sheets

(56) References Cited

FOREIGN PATENT DOCUMENTS

| WO | 2012043949 A1 | 4/2012 |
|---|---|---|
| WO | 2012172090 | 12/2012 |

OTHER PUBLICATIONS

Abderhalden-Kaufmann-Lignac, 2018, https://www.medigoo.com/articles/abderhalden-kaufmann-lignac-syndrome/.*
Renal-Disorder, 2018, https://medlineplus.gov/ency/article/001265.htm.*
Kidney-Disease, 2018, http://www.kidney.nyc/types-of-kidney-disease/.*
Seizure_Medication_List, 2018, https://www.epilepsy.com/learn/treating-seizures-and-epilepsy/seizure-medication-list.*
Medications_for_Neuropathic_Pain, 2018, https://www.spine-health.com/treatment/pain-management/medications-neuropathic-pain.*
Marks et al., Psychiatry Invest 2009, 6, 55-58.*
Clonazepam_—_Wikipedia, 2018, https://en.wikipedia.org/wiki/Clonazepam.*
Yang et al., Molecular Diversity (2011), 15(2), 361-372.*
Cancer_Prevention, 2018, https://www.mayoclinic.org/healthy-lifestyle/adult-health/in-depth/cancer-prevention/art-20044816.*
Parkisons_Disease_Prevention, 2018, https://www.mayoclinic.org/diseases-conditions/parkinsons-disease/symptoms-causes/syc-20376055.*
Kaulaskar et al., 2012, Zhongxiyi Jiehe Xuebao, 10(12), 1482-1489.*
Aswar et al., Pharmacology Biochemistry and Behavior, 2014, 124, 101-107.*
Pal et al. International Joural of Pharmaceuticals Analysis, vol. 2, Issue 2, pp. 01-04 (2010).
Kaulaskar, et al. Journal of Chinese Integrative Medicine, vol. 10, No. 12, pp. 1482-1489 (2012).
Todorovic, et al. Neuron, vol. 31, No. 1, pp. 75-85 (2001).
Adam, et al. Bioorganic & Medicinal Chemistry Letters, vol. 22, No. 8, pp. 2932-2937 (2012).
Huang, et al. The Journal of Pharmacology and Experimental Therapeutics, vol. 309, No. 1, pp. 193-199 (2004).
International Search Report issued in PCT/JP2014/063102 dated Aug. 5, 2014 (2 pages).
International Preliminary Report on Patentability and Written Opinion, PCT/JP2014/063102, dated Nov. 26, 2015 (8 pages).
Akazawa et al. Chemistry and Biodiversity, vol. 9, No. 6, pp. 1045-1054, 2012.
Si-Ahmed et al. Journal of Pharmaceutical and Biomedical Analysis, vol. 51, No. 1, pp. 225-229, 2010.
Wang et al. Natural Product Research, vol. 24, No. 13, pp. 1206-1213, Aug. 15, 2010.
Jeong et al. Biological & Pharmaceutical Bulletin, vol. 31, No. 10, pp. 1964-1967, 2008.
Peng et al. Journal of Chromatography A, vol. 1115, No. 1-2, pp. 103-111, 2006.
Trost et al."Regioselectivity in lithiation of t-butyldimethylsiloxy-3,5-dimethoxybenzene. A synthesis of the trimethyl ether of sophoraflavanone A", Tetrahedron Letters, vol. 26, No. 2, 1985, pp. 123-126, total 4 pages.
Phommart et al."Constituents of the Leaves of Macaranga tanarius", Journal of Natural Products, vol. 68, No. 6, 2005, pp. 927-930, total 4 pages.
Jain et al."Synthesis of carpachromene and related isopentenylated derivatives of apigenin", Tetrahedron, vol. 34, No. 24, 1978, pp. 3569-3573, total 5 pages.
Rao et al."A revised structure for crotaramosmin from crotolaria ramosissima ", vol. 61, No. 9, 1998, pp. 1148-1149, total 2 pages.
Sheu et al."Cytotoxic flavonoids and new chromenes from *Ficus formosana* f. *formosana*", Planta Medica, vol. 71, No. 12, 2005, pp. 1165-1167, total 3 pages.
Narender et al."BF3•OEt2 mediated regioselective deacetylation of polyacetoxyacetophenones and its application in the synthesis of natural products", Tetrahedron Letters, vol. 49, Issue 28, 2008, pp. 4409-4415, total 7 pages.
Seo et al."Cytotoxic prenylated flavanones from Monotes engleri", Phytochemistry, vol. 45, No. 3,1997, pp. 509-515, total 7 pages.
The Extended European Search Report of European Application No. 14801611.6, dated Nov. 8, 2016, total 11 pages.
Dawson et al., 1911, caplus an 1911 :5996.
Jain et al., 1970, caplus an 1970:455759.
Kim et al.: "Effects of Sophoraflavanone G, a Prenylated Flavonoid from Sophora Flavescens, on Cyclooxygenase-2 an In Vivo Inflamatory Response"; Archives of Pharmacal Research, 2002, vol. 25(3), pp. 329-335.
Stevens et al.: "Inhibition of Peroxynitrite-Medicated LDL Oxidation by Prenylated Flavonoids: The α,β-Unsaturated Keto Functionality of 2'-Hydroxychalcones as a Novel Antioxidant Pharmacophore"; Chemical Research in Toxicology, 2003, vol. 16(10), pp. 1277-1286.
Office Action issued in European Application No. 14801611.6 dated Sep. 18, 2018.

\* cited by examiner

[Fig. 1]
T-type calcium channel inhibitory action of sophoraflavanone G in whole-cell patch clamp method
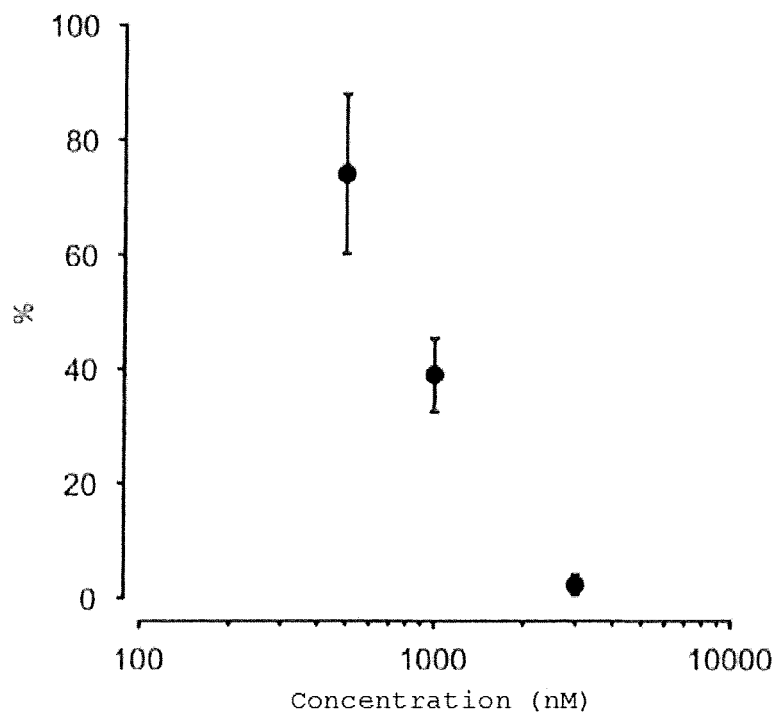
%: Ratio of T-channel current at addition of each compound to T-channel current at addition of solvent (DMSO)

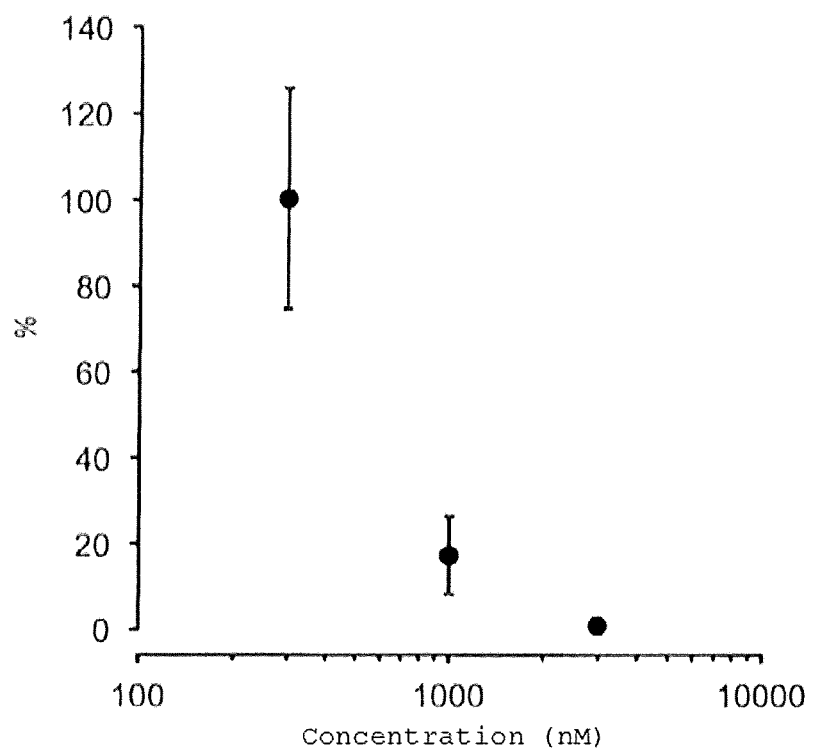
[Fig. 2]
T-type calcium channel inhibitory action of 6-prenylnaringenin in whole-cell patch clamp method
%: Ratio of T-channel current at addition of each compound to T-channel current at addition of solvent (DMSO)

[Fig. 3]
T-type calcium channel inhibitory action of
8-prenylnaringenin in whole-cell patch clamp method
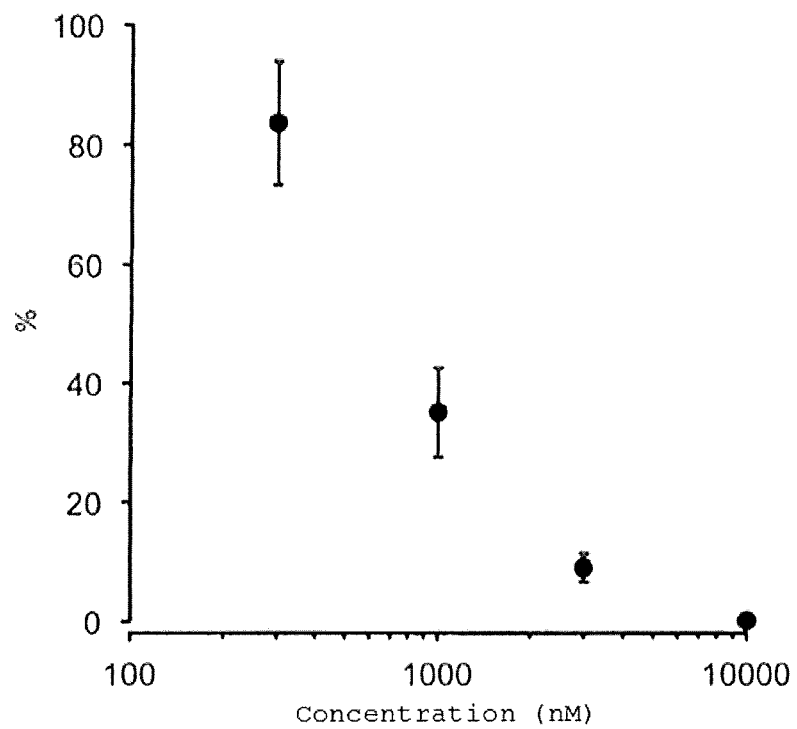
%: Ratio of T-channel current at addition of each compound
to T-channel current at addition of solvent (DMSO)

[Fig. 4]
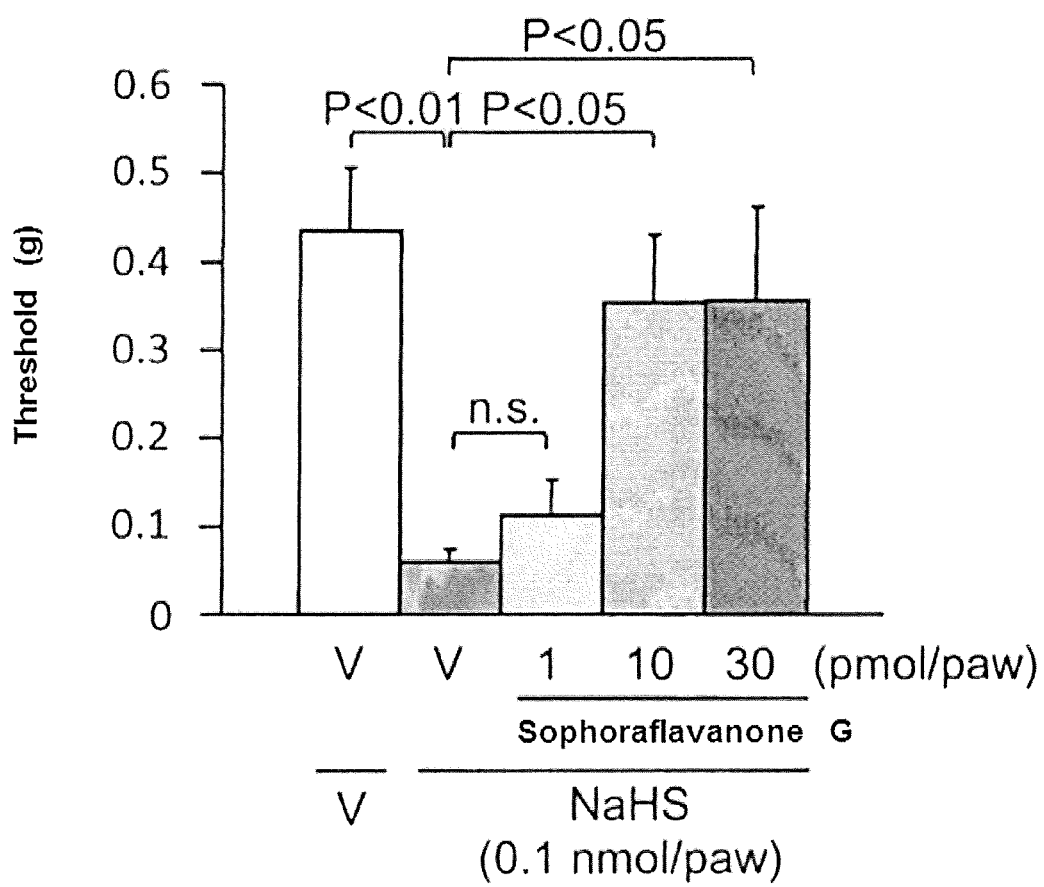

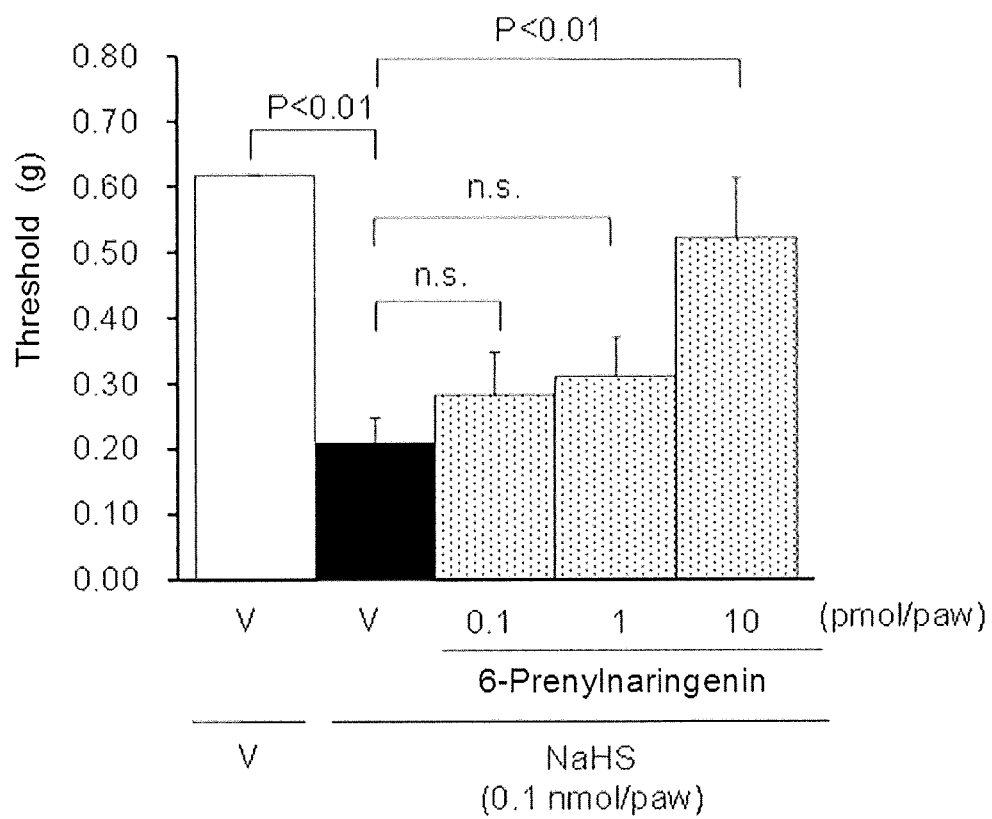
[Fig. 5]

[Fig. 6]
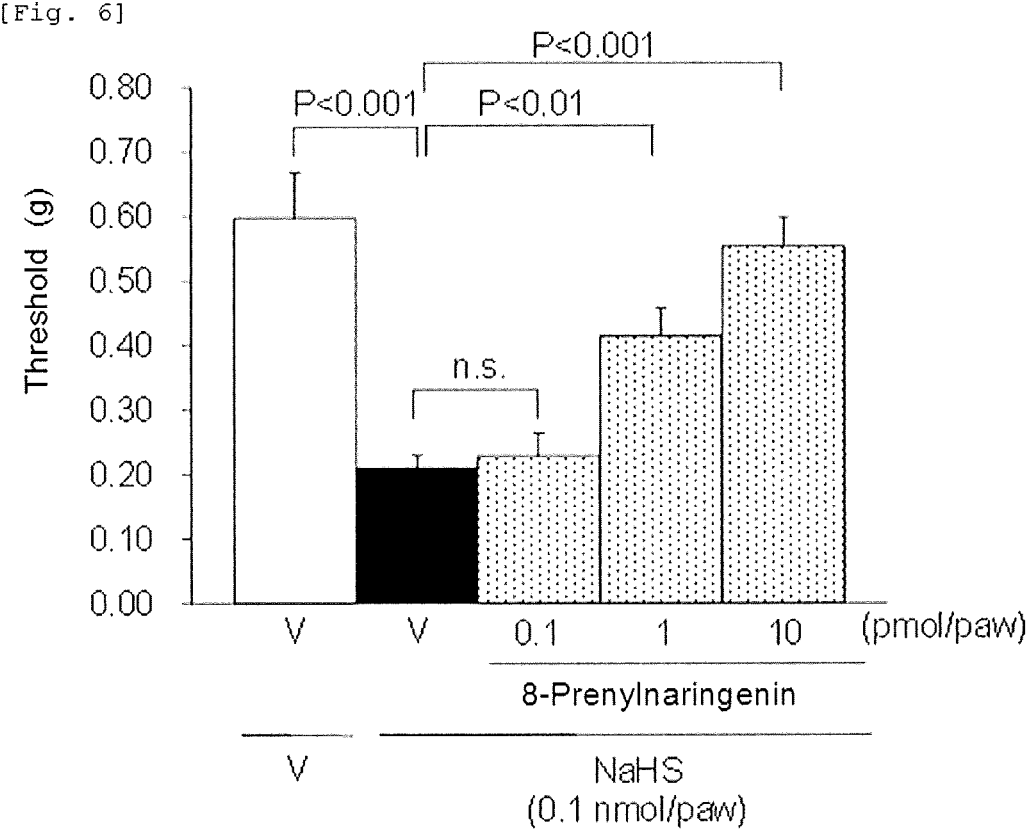

[Fig. 7]
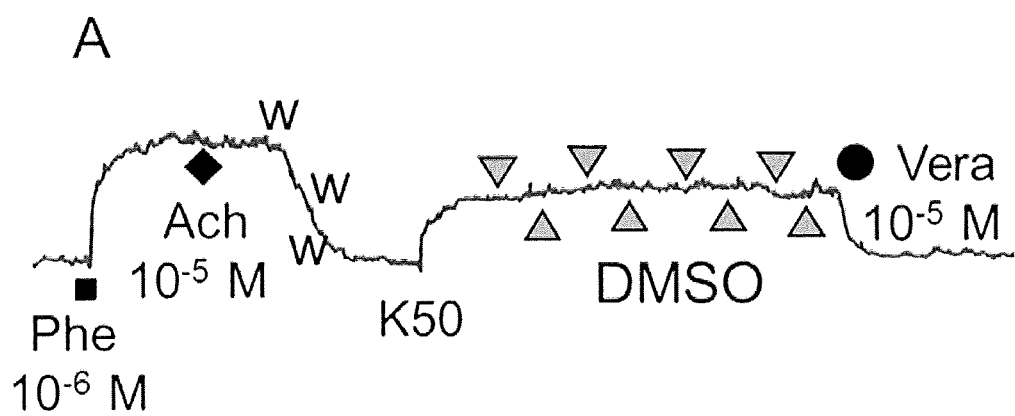

[Fig. 8]
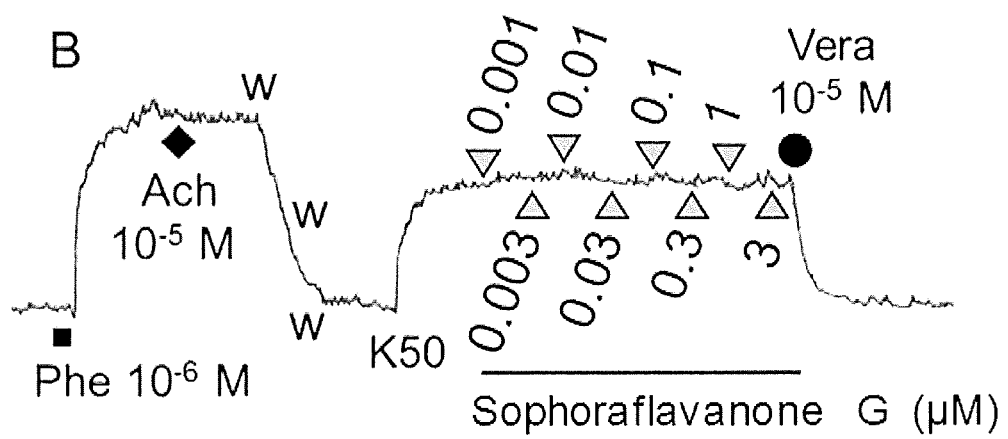

[Fig. 9]
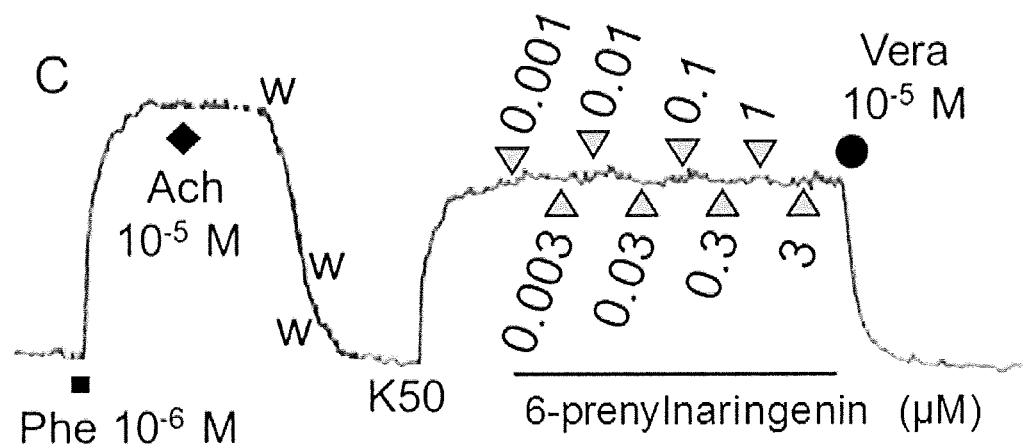

[Fig. 10]
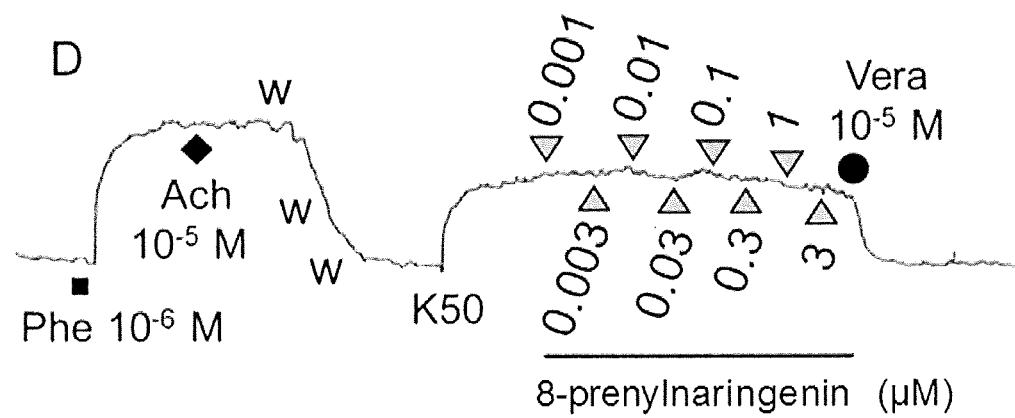

T-TYPE CALCIUM CHANNEL INHIBITOR

TECHNICAL FIELD

The present invention relates to a T-type calcium channel inhibitor which is a flavanone compound. The present invention also relates to a pharmaceutical product containing the T-type calcium channel inhibitor, and a therapeutic agent or prophylactic agent for diseases, the effective action of which is a T-type calcium channel inhibitory action.

BACKGROUND ART

Ion channels are channels extending through the cell membrane, and are classified broadly into two types: ligand-dependent channels and potential-dependent channels. In recent years, as a type of mechanism of neuropathic pains, a potential-dependent sodium channel and a potential-dependent calcium channel have been found as a target. As drugs targeting a potential-dependent sodium channel, for example, lidocaine, carbamazepine, lamotrigine, mexiletine and the like are known. As drugs targeting a potential-dependent calcium channel, for example, gabapentin pregabalin, ziconotide and the like are known.

The neuropathic pain is refractory, and has the problem of inadequate response to existing analgesic drugs. The efficacy of even an established drug therapy is difficult to predict accurately, and other drugs must often be used in combination. In "Guidelines for the Pharmacologic Management of Neuropathic Pain" from Japan Society of Pain Clinicians, high-potential-activated calcium channel inhibitors are listed as a primary choice, but in many cases, an adequate therapeutic effect is not obtained. These inhibitors have a problem of causing side effects such as lightheadedness.

Potential-dependent calcium channels are classified into two types: high-potential-activated types and low-potential-activated types based on a difference in activation and deactivation potentials. L-type, N-type, P/Q-type and R-type calcium channels are activated by large depolarization, and therefore classified as high-potential-activated calcium channels. On the other hand, T-type calcium channels are activated by small depolarization, and therefore classified as low-potential-activated calcium channels.

Recently, T-type calcium channels have been reported to be involved in onset and development of a neuropathic pain, and potential of T-type calcium channel inhibitors as therapeutic agents for the pain has been suggested. Examples of the T-type calcium channel inhibitor include mibefradil (see, for example, Todorovic, Neuron, 2001, 31 (1), p. 75-85 (Non-Patent Document 1)), ethosuximide, and (1S,2S)-2-[2-[3-(1H-benzimidazol-2-yl)propyl]methylamino]ethyl]-6-fluoro-1,2,3,4-tetrahydro-1-(1-methylethyl)-2-naphthalenyl-cyclopropane carboxylate hydrochloride (NNC55-0396) (see, for example, Huang, J Pharmacol Exp Ther., 309(1), p. 193-199 (Non-Patent Document 2)). Thus, some compounds have already been found as T-type calcium channel inhibitors, but further studies on new T-type calcium channel inhibitors are required in view of side effects etc.

Flavanone compounds having a flavanone backbone are compounds contained in natural extracts etc. These flavanone compounds have been found to have various drug efficacies. For example, it has been found that sophoraflavanone G which is a type of flavanone compound can be used as an antibacterial agent having an inhibitory action on proliferation of *Propionibacterium acnes* and *Pityrosporum ovale* (Japanese Patent No. 3327699 (Patent Document 1)). For example, Japanese Patent No. 4393062 (Patent Document 2) discloses that extracts from *Sophora*, which contain a flavone selected from the group consisting of 8-prenylnaringenin, kushenol X, 8-prenylkaempferol, leachianone G and kushenol E, an alkaloid, an isoflavone, a chalcone and a pterocarpan are capable of preventing and treating disease conditions caused by abnormal metabolism of estrogen. On the other hand, it is not disclosed that the flavanone compound has a T-type calcium channel inhibitory action.

PRIOR ART DOCUMENTS

Patent Documents

Patent Document 1: Japanese Patent No. 3327699
Patent Document 2: Japanese Patent No. 4393062

Non-Patent Documents

Non-Patent Document 1: Todorovic, Neuron, 2001, 31(1), p. 75-85
Non-Patent Document 2: Huang, J Pharmacol Exp Ther., 2004, 309(1), p. 193-199

SUMMARY OF INVENTION

Problem to be Solved by the Invention

The present inventors have searched for a new T-type calcium channel inhibitor towards development of a new analgesic drug targeting a T-type calcium channel for therapeutic. As a result, the present inventors have found that a flavanone compound strongly inhibits a T-type calcium channel, leading to completion of the present invention.

An object of the present invention is to provide a T-type calcium channel inhibitor which is a flavanone compound; a pharmaceutical product containing the T-type calcium channel inhibitor; and a therapeutic agent or prophylactic agent for diseases, the effective action of which is a T-type calcium channel inhibitory action.

Means for Solving the Problem

The present invention provides a T-type calcium channel inhibitor, wherein the T-type calcium channel inhibitor is a compound represented by the formula (1):

[Chemical Formula 1]

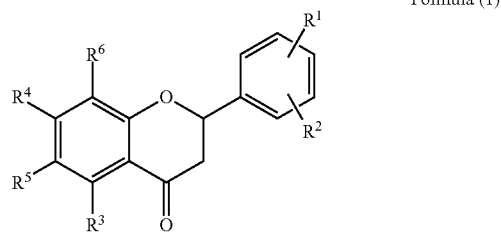

Formula (1)

[wherein
each of $R^1$ and $R^2$ independently represents H, —OH, or —OR$^{11}$ wherein $R^{11}$ represents a $C_{1-3}$ alkyl group;
each of $R^3$ and $R^4$ independently represents H, —OH, or —OR$^{12}$ wherein $R^{12}$ represents a $C_{1-3}$ alkyl group; and
each of $R^5$ and $R^6$ independently represents H, a halogen atom, a $C_{1-10}$ alkyl group, a $C_{2-6}$ alkenyl group, a $C_{2-6}$ alkynyl group, a phenyl group (the phenyl group may be substituted with a $C_{1-6}$ alkoxy group or a halogen atom), a —$C_{1-3}$ alkyl-phenyl group (the phenyl group may be substituted with a $C_{1-6}$ alkyloxy group or a halogen atom), or a $C_{10-50}$ prenyl group], a pharmaceutically acceptable salt of the compound, or a solvate of the compound. The above-mentioned object is hereby achieved.

Preferably, each of $R^1$ and $R^2$ independently represents H, —OH, or —$OR^{11}$ wherein $R^{11}$ represents a $C_{1-3}$ alkyl group; each of $R^3$ and $R^4$ independently represents H, —OH, or —$OR^{12}$ wherein $R^{12}$ represents a $C_{1-3}$ alkyl group; and each of $R^5$ and $R^6$ independently represents H, a $C_{1-10}$ alkyl group, a $C_{2-6}$ alkenyl group or a $C_{10-50}$ prenyl group.

More preferably, each of $R^1$ and $R^2$ independently represents H or —OH; each of $R^3$ and $R^4$ independently represents —OH or —$OR^{12}$ wherein $R^{12}$ represents a $C_{1-3}$ alkyl group; and each of $R^5$ and $R^6$ independently represents H, a $C_{1-10}$ alkyl group, a $C_{2-6}$ alkenyl group or a $C_{10-50}$ prenyl group.

Further preferably, each of $R^1$ and $R^2$ independently represents H or —OH; each of $R^3$ and $R^4$ independently represents —OH; and each of $R^5$ and $R^6$ independently represents H, a $C_{2-6}$ alkenyl group, a 3,7-dimethyl-2,6-octadienyl group or a 5-methyl-2-(1-methylethenyl)-4-hexenyl group.

The present invention also provides a pharmaceutical product containing the T-type calcium channel inhibitor, and a therapeutic agent or prophylactic agent for neuropathic pains, which contains the T-type calcium channel inhibitor.

Effect of the Invention

The T-type calcium channel inhibitor according to the present invention which is a flavanone compound has an excellent T-type calcium channel inhibitory action. The T-type calcium channel inhibitor according to the present invention is very useful in the fields of, for example, medical cares, pharmaceutical products and prophylactic agents.

BRIEF DESCRIPTION OF DRAWINGS

FIG. 1 is a graph chart showing experimental results of Example 1.
FIG. 2 is a graph chart showing experimental results of Example 2.
FIG. 3 is a graph chart showing experimental results of Example 3.
FIG. 4 is a graph chart showing experimental results of Example 4.
FIG. 5 is a graph chart showing experimental results of Example 5.
FIG. 6 is a graph chart showing experimental results of Example 6.
FIG. 7 is a graph chart showing effects of DMSO on K50-induced contraction in a ring preparation of a rat aorta.
FIG. 8 is a graph chart showing effects of sophoraflavanone G on K50-induced contraction in a ring preparation of a rat aorta.
FIG. 9 is a graph chart showing effects of 6-prenylnaringenin on K50-induced contraction in a ring preparation of a rat aorta.
FIG. 10 is a graph chart showing effects of 8-prenylnaringenin on K50-induced contraction in a ring preparation of a rat aorta.

MODE FOR CARRYING OUT THE INVENTION

In this specification, "n-" denotes normal, "i-" denotes "iso," "s-" denotes "secondary," "t-" denotes "tertiary," and "c-" denotes "cyclo." The substituents will be described below.

Examples of the halogen atom include a fluorine atom, a chlorine atom, a bromine atom and an iodine atom.

The $C_{1-3}$ alkyl group may be a linear $C_{1-3}$ alkyl group, a branched $C_3$ alkyl group or a $C_3$ cycloalkyl group, and examples thereof include a methyl group, an ethyl group, an n-propyl group, an i-propyl group and a c-propyl group.

The $C_{1-3}$ alkyl group may be substituted or unsubstituted. Examples of the substituent include an alkoxy group, an aryloxy group, a sulfhydryl group, an alkylthio group, an arylthio group, a halogen atom, a hydroxyl group, a fluoroalkyl group, a perfluoroalkyl group, an amino group, an aminoalkyl group, a disubstituted amino group, a hydroxyalkyl group, a carboxyalkyl group and a carboxyl group.

The $C_{1-10}$ alkyl group may be a linear $C_{1-10}$ alkyl group, a branched $C_{3-10}$ alkyl group or a $C_{3-10}$ cycloalkyl group, and examples thereof include a methyl group, an ethyl group, an n-propyl group, an i-propyl group, a c-propyl group, an n-butyl group, an i-butyl group, an s-butyl group, a t-butyl group, a c-butyl group, an n-pentyl group, a 1-methyl-n-butyl group, a 2-methyl-n-butyl group, a 3-methyl-n-butyl group, a 1,1-dimethyl-n-propyl group, a c-pentyl group, a 2-methyl-c-butyl group, an n-hexyl group, a 1-methyl-n-pentyl group, a 2-methyl-n-pentyl group, a 1,1-dimethyl-n-butyl group, a 1-ethyl-n-butyl group, a 1,1,2-trimethyl-n-propyl group, a c-hexyl group, a 1-methyl-c-pentyl group, 1-ethyl-c-butyl group, a 1,2-dimethyl-c-butyl group, an n-heptyl group, a 1-methyl-n-hexyl group, a 2-methyl-n-hexyl group, a 1,1-dimethyl-n-pentyl group, a 1-ethyl-n-pentyl group, a 1,1,2-trimethyl-n-butyl group, a c-heptyl group, a 1-methyl-c-hexyl group, a 2-methyl-c-hexyl group, a 3-methyl-c-hexyl group, a 1-ethyl-c-pentyl group, a 2-ethyl-c-pentyl group, a 1,2-dimethyl-c-pentyl group, a 1,3-dimethyl-c-pentyl group, a 1,4-dimethyl-c-pentyl group, an n-octyl group, a 1-methyl-n-heptyl group, a 2-methyl-n-heptyl group, a 1,1-dimethyl-n-hexyl group, a 1-ethyl-n-hexyl group, a 1,1,2-trimethyl-n-pentyl group, a c-octyl group, a 1-methyl-c-heptyl group, a 2-methyl-c-heptyl group, a 3-methyl-c-heptyl group, a 1-ethyl-c-hexyl group, a 2-ethyl-c-hexyl group, a 1,2-dimethyl-c-hexyl group, a 1,3-dimethyl-c-hexyl group, a 1,4-dimethyl-c-hexyl group, an n-nonyl group, a 1-methyl-n-octyl group, a 2-methyl-n-octyl group, a 1,1-dimethyl-n-heptyl group, a 1-ethyl-n-heptyl group, a 1,1,2-trimethyl-n-hexyl group, a c-nonyl group, a 1-methyl-c-octyl group, a 2-methyl-c-octyl group, a 3-methyl-c-octyl group, a 1-ethyl-c-heptyl group, a 2-ethyl-c-heptyl group, a 1,2-dimethyl-c-heptyl group, a 1,3-dimethyl-c-heptyl group, a 1,4-dimethyl-c-heptyl group, an n-decyl group, a 1-methyl-n-nonyl group, a 2-methyl-n-nonyl group, a 1,1-dimethyl-n-octyl group, a 1-ethyl-n-octyl group, a 1,1,2-trimethyl-n-heptyl group, a c-decyl group, a 1-methyl-c-nonyl group, a 2-methyl-c-nonyl group, a 3-methyl-c-nonyl group, a 1-ethyl-c-octyl group, a 2-ethyl-c-octyl group, a 1,2-dimethyl-c-octyl group, a 1,3-dimethyl-c-octyl group, a 1,4-dimethyl-c-octyl group, a c-pentyl-$C_{1-5}$ alkyl group, a c-hexyl-$C_{1-4}$ alkyl group, a c-heptyl-$C_{1-3}$ alkyl group and a c-octyl-$C_{1-2}$ alkyl group.

The $C_{1-10}$ alkyl group may be substituted or unsubstituted. Examples of the substituent include an alkoxy group, an aryloxy group, a sulfhydryl group, an alkylthio group, an arylthio group, a halogen atom, a hydroxyl group, a fluoroalkyl group, a perfluoroalkyl group, an amino group, an aminoalkyl group, a disubstituted amino group, a hydroxyalkyl group, a carboxyalkyl group and a carboxyl group.

The $C_{2-6}$ alkenyl group includes one that is linear or branched, and examples thereof include an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethylethenyl group, a 1-methyl-1-propenyl group, a 1-methyl-2-propenyl group, a 1-pentenyl group, a 2-pentenyl group, a 3-pentenyl group, a 4-pentenyl group, a 1-n-propylethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-i-propylethenyl group, a 1,2-dimethyl-1-propenyl group, a 1,2-dimethyl-2-propenyl group, a 1-hexenyl group, a 2-hexenyl group, a 3-hexenyl group, a 4-hexenyl group, a 5-hexenyl group, a 1-methyl-1-pentenyl group, a 1-methyl-2-pentenyl group, a 1-methyl-3-pentenyl group, a 1-methyl-4-pentenyl group, a 1-n-butylethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-s-butylethenyl group, a 1,3-dimethyl-1-butenyl group, a 1,3-dimethyl-2-butenyl group, a 1,3-dimethyl-3-butenyl group, a 1-i-butylethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-i-propyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-t-butylethenyl group, a 1-methyl-1-ethyl-2-propenyl group, a 1-ethyl-2-methyl-1-propenyl group, a 1-ethyl-2-methyl-2-propenyl group, a 1-i-propyl-1-propenyl group and a 1-i-propyl-2-propenyl group.

Among these $C_{2-6}$ alkenyl groups, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-i-propylethenyl group, a 1,2-dimethyl-1-propenyl group, a 1,2-dimethyl-2-propenyl group, a 1-hexenyl group, a 2-hexenyl group, a 3-hexenyl group, a 4-hexenyl group, a 5-hexenyl group and the like may be more preferable.

The $C_{2-6}$ alkenyl group may be substituted or unsubstituted. Examples of the substituent include an alkoxy group, an aryloxy group, a sulfhydryl group, an alkylthio group, an arylthio group, a halogen atom, a hydroxyl group, a fluoroalkyl group, a perfluoroalkyl group, an amino group, an aminoalkyl group, a disubstituted amino group, a hydroxyalkyl group, a carboxyalkyl group and a carboxyl group.

The $C_{2-6}$ alkynyl group includes one that is linear or branched, and examples thereof include an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-2-butynyl group, a 1-methyl-3-butynyl group, a 2-methyl-3-butynyl group, a 3-methyl-1-butynyl group, a 1,1-dimethyl-2-propynyl group, a 2-ethyl-2-propynyl group, a 1-hexynyl group, a 2-hexynyl group, a 3-hexynyl group, a 4-hexynyl group, a 5-hexynyl group, a 1-methyl-2-pentynyl group, a 1-methyl-3-pentynyl group, a 1-methyl-4-pentynyl group, a 2-methyl-3-pentynyl group, a 2-methyl-4-pentynyl group, a 3-methyl-1-pentynyl group, a 3-methyl-4-pentynyl group, a 4-methyl-1-pentynyl group, a 4-methyl-2-pentynyl group, a 1,1-dimethyl-2-butynyl group, a 1,1-dimethyl-3-butynyl group, a 1,2-dimethyl-3-butynyl group, a 2,2-dimethyl-3-butynyl group, a 3,3-dimethyl-1-butynyl group, a 1-ethyl-2-butynyl group, a 1-ethyl-3-butynyl group, a 1-n-propyl-2-propynyl group, a 2-ethyl-3-butynyl group, a 1-methyl-1-ethyl-2-propynyl group and a 1-i-propyl-2-propynyl group.

The $C_{2-6}$ alkynyl group may be substituted or unsubstituted. Examples of the substituent include an alkoxy group, an aryloxy group, a sulfhydryl group, an alkylthio group, an arylthio group, a halogen atom, a hydroxyl group, a fluoroalkyl group, a perfluoroalkyl group, an amino group, an aminoalkyl group, a disubstituted amino group, a hydroxyalkyl group, a carboxyalkyl group and a carboxyl group.

Examples of the $C_{1-6}$ alkyloxy group include a methyloxy group, an ethyloxy group, an n-propyloxy group, an i-propyloxy group, an n-butyloxy group, an i-butyloxy group, an s-butyloxy group, a t-butyloxy group, an n-pentyloxy group and an n-hexyloxy group.

The prenyl group generally means a generic name of structural units composed of isoprene units having 5 carbon atoms. In this specification, the prenyl group means a $C_{10-50}$ prenyl group, i.e. a prenyl group other than a dimethylallyl group, the number of carbon atoms of which is 5. Specific examples of the $C_{10-50}$ prenyl group include a 3,7-dimethyl-2,6-octadienyl group (number of carbon atoms: 10, geranyl group), a 5-methyl-2-(1-methylethenyl)-4-hexenyl group (number of carbon atoms: 10), a farnesyl group (number of carbon atoms: 15), a geranylgeranyl group (number of carbon atoms: 20), a geranylfarnesyl group (number of carbon atoms: 25), a hexaprenyl group (number of carbon atoms: 30), a heptaprenyl group (number of carbon atoms: 35), an octaprenyl group (number of carbon atoms: 40), a nonaprenyl group (number of carbon atoms: 45) and a decaprenyl group (number of carbon atoms: 50).

The prenyl group may be substituted or unsubstituted. Examples of the substituent include an alkoxy group, an aryloxy group, a sulfhydryl group, an alkylthio group, an arylthio group, a halogen atom, a hydroxyl group, a fluoroalkyl group, a perfluoroalkyl group, an amino group, an aminoalkyl group, a disubstituted amino group, a hydroxyalkyl group, a carboxyalkyl group and a carboxyl group.

The T-type calcium channel inhibitor according to the present invention has a structure as shown in the following formula (1).

[Chemical formula 2]

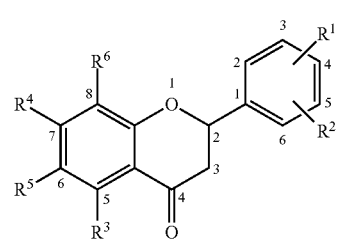

Formula (1)

In the formula (1),
each of $R^1$ and $R^2$ independently represents H, —OH, or —$OR^{11}$ wherein $R^{11}$ represents a $C_{1-3}$ alkyl group;

each of $R^3$ and $R^4$ independently represents H, —OH, or —OR$^{12}$ wherein $R^{12}$ represents a $C_{1-3}$ alkyl group; and
each of $R^5$ and $R^6$ independently represents H, a halogen atom, a $C_{1-10}$ alkyl group, a $C_{2-6}$ alkenyl group, a $C_{2-6}$ alkynyl group, a phenyl group (the phenyl group may be substituted with a $C_{1-6}$ alkoxy group or a halogen atom), a —$C_{1-3}$ alkyl-phenyl group (the phenyl group may be substituted with a $C_{1-6}$ alkyloxy group or a halogen atom), or a $C_{10-50}$ prenyl group.

More preferably, each of $R^1$ and $R^2$ independently may represent H or —OH. Further preferably, in the formula (1), $R^1$ may be at the 4-position and may be —OH, and $R^2$ may be at the 2-position and may be —OH or H.

More preferably, each of $R^3$ and $R^4$ independently may represent —OH or —OR$^{12}$ wherein $R^{12}$ represents a $C_{1-3}$ alkyl group. Further preferably, each of $R^3$ and $R^4$ independently may represent —OH.

More preferably, each of $R^5$ and $R^6$ independently may represent H, a $C_{1-10}$ alkyl group, a $C_{2-6}$ alkenyl group or a $C_{10-50}$ prenyl group. Here, examples of the preferred $C_{2-6}$ alkenyl group as $R^5$ and $R^6$ include a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-i-propylethenyl group, a 1,2-dimethyl-1-propenyl group, a 1,2-dimethyl-2-propenyl group, a 1-hexenyl group, a 2-hexenyl group, a 3-hexenyl group, a 4-hexenyl group and a 5-hexenyl group. Examples of the especially preferred $C_{2-6}$ alkenyl group include a 3-methyl-2-butenyl group. Examples of the preferred $C_{10-50}$ prenyl group as $R^5$ and $R^6$ include a 3,7-dimethyl-2,6-octadienyl group (number of carbon atoms: 10, geranyl group), a 5-methyl-2-(1-methylethenyl)-4-hexenyl group (number of carbon atoms: 10) and a farnesyl group (number of carbon atoms: 15). The $C_{10-50}$ prenyl group as $R^5$ and $R^6$ is especially preferably a 3,7-dimethyl-2,6-octadienyl group or a 5-methyl-2-(1-methylethenyl)-4-hexenyl group.

Particularly preferably, each of $R^5$ and $R^6$ independently represents H, a $C_{2-6}$ alkenyl group, a 3,7-dimethyl-2,6-octadienyl group or a 5-methyl-2-(1-methylethenyl)-4-hexenyl group. Especially preferably, for example, one of $R^5$ and $R^6$ is H, and the other is a $C_{2-6}$ alkenyl group, a 3,7-dimethyl-2,6-octadienyl group or a 5-methyl-2-(1-methylethenyl)-4-hexenyl group.

Preferred compounds among those represented by the above formula (1) include compounds in which in the above formula (1),
each of $R^1$ and $R^2$ independently represents H, —OH, or —OR$^{11}$ wherein $R^{11}$ represents a $C_{1-3}$ alkyl group;
each of $R^3$ and $R^4$ independently represents H, —OH, or —OR$^{12}$ wherein $R^{12}$ represents a $C_{1-3}$ alkyl group; and
each of $R^5$ and $R^6$ independently represents H, a $C_{1-10}$ alkyl group, a $C_{2-6}$ alkenyl group or a $C_{10-50}$ prenyl group.

More preferred compounds among those represented by the above formula (1) include compounds in which in the above formula (1),
each of $R^1$ and $R^2$ independently represents H or —OH;
each of $R^3$ and $R^4$ independently represents —OH or —OR$^{12}$ wherein $R^{12}$ represents a $C_{1-3}$ alkyl group; and
each of $R^5$ and $R^6$ independently represents H, a $C_{1-10}$ alkyl group, a $C_{2-6}$ alkenyl group or a $C_{10-50}$ prenyl group.

Further preferred compounds among those represented by the above formula (1) include compounds in which in the above formula (1),
each of $R^1$ and $R^2$ independently represents H or —OH; each of $R^3$ and $R^4$ represent —OH; and
each of $R^5$ and $R^6$ independently represents H, a $C_{2-6}$ alkenyl group, a 3,7-dimethyl-2,6-octadienyl group or a 5-methyl-2-(1-methylethenyl)-4-hexenyl group.

Especially preferred compounds among those represented by the above formula (1) include compounds in which in the above formula (1),
$R^1$ is at the 4-position and is —OH, and $R^2$ is at the 2-position and is H or —OH;
each of $R^3$ and $R^4$ represents —OH; and
each of $R^5$ and $R^6$ independently represents H, a $C_{2-6}$ alkenyl group, a 3,7-dimethyl-2,6-octadienyl group or a 5-methyl-2-(1-methylethenyl)-4-hexenyl group. Herein, especially preferably, one of $R^5$ and $R^6$ may be H, and the other may be a $C_{2-6}$ alkenyl group, a 3,7-dimethyl-2,6-octadienyl group or a 5-methyl-2-(1-methylethenyl)-4-hexenyl group.

Such a compound may also be referred to as naringenin compound.

In the present invention, specific examples of the compound represented by the above formula (1) include the following compounds:

(2S)-5,7-dihydroxy-2,3-dihydro-2-(2,4-dihydroxyphenyl)-8-[(R)-5-methyl-2-(1-methylethenyl)-4-hexenyl]-4H-1-benzopyran-4-one (sophoraflavanone G);

(2S)-5,7-dihydroxy-2,3-dihydro-2-(2,4-dihydroxyphenyl)-6-[(R)-5-methyl-2-(1-methylethenyl)-4-hexenyl]-4H-1-benzopyran-4-one;

(2S)-5,7-dihydroxy-2,3-dihydro-2-(4-hydroxyphenyl)-8-(3-methyl-2-butenyl)-4H-1-benzopyran-4-one (8-prenylnaringenin);

(2S)-5,7-dihydroxy-2,3-dihydro-2-(4-hydroxyphenyl)-6-(3-methyl-2-butenyl)-4H-1-benzopyran-4-one (6-prenylnaringenin);

(2S)-5,7-dihydroxy-2-(4-hydroxyphenyl)-2,3-dihydro-chromen-4-one (naringenin);

(2S)-2-(3,4-dihydroxyphenyl)-2,3-dihydro-7-hydroxy-4H-1-benzopyran-4-one (butyne);

(2S)-2-(3,4-dihydroxyphenyl)-2,3-dihydro-5,7-dihydroxy-4H-1-benzopyran-4-one (eriodictyol);

5,7-dihydroxy-2-phenyl-2,3-dihydro-4H-chromen-4-one (pinocembrin);

(2S)-5,7-dihydroxy-2-(3-hydoxy-4-methoxyphenyl)-2,3-dihydro-4H-chromen-4-one (hesperetin);

(2S)-5,7-dihydroxy-2-(4-hydoxy-3-methoxyphenyl)-2,3-dihydrochromen-4-one (homoeriodictyol);

(2S)-5,7-dihydroxy-2-(4-methoxyphenyl)-2,3-dihydro-chromen-4-one (isosakuranetin);

(2S)-5-hydroxy-2-(4-hydroxyphenyl)-7-methoxy-2,3-dihydrochromen-4-one (sakuranetin);

(2S)-2-(3,4-dihydroxyphenyl)-5-hydroxy-7-methoxy-2,3-dihydro-4H-chromen-4-one (sterubin);

(2S)-5,7-dihydroxy-2,3-dihydro-2-(2,4-dihydroxyphenyl)-8-(3-methyl-2-butenyl)-4H-1-benzopyran-4-one (leachianone G);

(2S)-5,7-dihydroxy-2,3-dihydro-2-(2,4-dihydroxyphenyl)-6,8-bis(3-methyl-2-butenyl)-4H-1-benzopyran-4-one (kushenol E);

(2S)-5,7-dihydroxy-2,3-dihydro-2-(2,4-dihydroxyphenyl)-8-(3,7-dimethyl-2,6-octadienyl)-4H-1-benzopyran-4-one (8-geranylnaringenin); and (2S)-5,7-dihydroxy-2,3-dihydro-2-(2,4-dihydroxyphenyl)-6-(3,7-dimethyl-2,6-octadienyl)-4H-1-benzopyran-4-one (6-geranylnaringenin).

Among the above-listed compounds, the following compounds may be especially preferable as the T-type calcium channel inhibitor according to the present invention:

(2S)-5,7-dihydroxy-2,3-dihydro-2-(2,4-dihydroxyphenyl)-8-[(R)-5-methyl-2-(1-methylethenyl)-4-hexenyl]-4H-1-benzopyran-4-one (sophoraflavanone G);

(2S)-5,7-dihydroxy-2,3-dihydro-2-(2,4-dihydroxyphenyl)-6-[(R)-5-methyl-2-(1-methylethenyl)-4-hexenyl]-4H-1-benzopyran-4-one;

(2S)-5,7-dihydroxy-2,3-dihydro-2-(4-hydroxyphenyl)-8-(3-methyl-2-butenyl)-4H-1-benzopyran-4-one (8-prenylnaringenin);

(2S)-5,7-dihydroxy-2,3-dihydro-2-(4-hydroxyphenyl)-6-(3-methyl-2-butenyl)-4H-1-benzopyran-4-one (6-prenylnaringenin); and (2S)-5,7-dihydroxy-2-(3-hydoxy-4-methoxyphenyl)-2,3-dihydro-4H-chromen-4-one (hesperetin).

The compound represented by the formula (1) may be prepared by separation and purification from natural products such as flesh of fruit, or leaves, roots, stalks and seeds of plants, or a commercially available product may be used. The compound may also be prepared by organic synthesis. For example, naringenin can be prepared by hydrolyzing naringin as a glycoside of naringenin using an enzyme or the like. Naringin can be separated from fruit skin, fruit juice and/or seeds of citrus fruits such as grapefruit using a general solvent extraction means or the like. The obtained naringin and naringinase are added in an aqueous solution to react with each other, whereby naringenin can be obtained (see, for example, "Handbook on Use of Enzymes," Michio KOZAKI, published by Chijinshokan Co., Ltd.). Commercially available naringenin from, for example, Sigma-Aldrich Corporation (St. Louis, Mo.) may also be used.

Sophoraflavanone G can be obtained by, for example, subjecting legume-derived phytoalexin to separation and purification by multi-stage chromatography or the like. Sophoraflavanone G can also be obtained by, for example, separation and purification in which Sophora root, i.e. a root of *Sophora flavescens*, is extracted with chloroform, and the obtained chloroform extract is subjected to silica gel column chromatography with a chloroform/methanol mixed liquid system and a hexane/acetone mixed liquid system.

8-Prenylnaringenin can be obtained as a 0.5% acetic acid/methanol (1:4) elution fraction by, for example, mixing naringenin and sodium methoxide in a methanol:ether mixed liquid, adding isopentenyl bromide therein, then distilling away the solvent, dissolving the mixture in ether, and then subjecting the solution to Dowex 1-X4 column chromatography. Commercially available 8-prenylnaringenin from Sigma-Aldrich Corporation (St. Louis, Mo.) may also be used.

6-Prenylnaringenin can be obtained as a 1.0% acetic acid/methanol (1:4) elution fraction by, for example, mixing naringenin and sodium methoxide in a methanol:ether mixed liquid, adding isopentenyl bromide therein, then distilling away the solvent, dissolving the mixture in ether, and then subjecting the solution to Dowex 1-X4 column chromatography. As another method, a hard resin from a hop plant is subjected to Dowex 1-X4 column chromatography to obtain 1.0% acetic acid/methanol (1:4), this acetic acid/methanol is solvent-fractionated with ether and a 10% aqueous sodium carbonate solution, and the obtained 10% aqueous sodium carbonate solution is made acidic with 1 N HCl, then extracted with ether, then washed with water, dried over sodium sulfate, then concentrated, and crystallized, whereby 6-prenylnaringenin can be obtained. Commercially available 6-prenylnaringenin from Sigma-Aldrich Corporation (St. Louis, Mo.) may also be used.

Hesperetin can be prepared by hydrolyzing hesperidin as a glycoside of hesperetin using an enzyme or the like. Hesperidin can be separated from, for example, fruit skin, fruit juice and/or seeds of citrus fruits such as Satsuma orange and summer orange using a general solvent extraction means or the like. Commercially available hesperidin from, for example, Hamari Company Ltd. may also be used. The obtained hesperidin and an enzyme such as hesperidinase, naringinase, rhamnosidase or glucosidase are added in an aqueous solution to react with each other, whereby hesperetin can be obtained.

Eriodictyol and sterubin can be obtained by, for example, subjecting extracts of natural products such as Yerba Santa, lemon and rosehip to separation and purification by multi-stage chromatography or the like.

Pinocembrin can be obtained by, for example, subjecting natural products such as honey and propolis to separation and purification by multi-stage chromatography or the like.

For each of these compounds, a commercially available product may be used. For example, hesperetin, eriodictyol and the like can be obtained from Sigma-Aldrich Corporation (St. Louis, Mo.).

In the T-type calcium channel inhibitor represented by the above formula (1) according to the present invention, the compound represented by the above formula (1) may be in the form of a salt. That is, a pharmaceutically acceptable salt of the compound represented by the above formula (1) can also be used as a T-type calcium channel inhibitor. Examples of the pharmaceutically acceptable salt include hydrochlorides, sulfates, methanesulfonates, hydrobromates, acetates, benzoates, tartrates, lactates, malates, salicylates, phosphates, maleates and fumarates.

In the T-type calcium channel inhibitor represented by the above formula (1) according to the present invention, the compound represented by the above formula (1) may be in the form of a solvate. The solvate is not particularly limited as long as it is pharmaceutically acceptable, and examples thereof may include hydrates, and alcoholates such as ethanolates.

The T-type calcium channel inhibitors according to the present invention also include prodrugs of the T-type calcium channel inhibitor represented by the above formula (1). The term "prodrug" means a compound which is converted into an activated form having a pharmacological action by hydrolysis in the body, for example, in blood. Examples of the pharmacologically acceptable prodrug are described in the documents: T. Higuchi and V. Stella, Prodrugs as Novel Drug Delivery Systems, "Bioreversible Carriers in Drug Design," edited by Edward B. Roche, American Pharmaceutical Association and Pergamon Press, A.C.S. Symposium Series, Vol. 14, (1987); and D. Fleisher, R. Bong and B. H. Stewart, "Improved oral drug delivery: Solubility limitations overcome by the use of prodrugs," Advanced Drug Delivery Reviews (1996) 19(2): 115-130. When the compound represented by the formula (1) has a hydroxyl group, examples of the prodrug include prodrugs such as acyloxy derivatives which are prepared by reacting an acyl halide, an acid anhydride or a halogenated alkyloxy carbonyl compound with the compound represented by the formula (1).

A therapeutic agent or prophylactic agent for diseases according to the present invention, the effective action of which is a T-type calcium channel inhibitory action, can be administered as an orally-administered agent such as a general tablet, capsule, powder, granule, pill or oral liquid (syrup), a transmucosal absorption agent such as a renal administration agent, a nasal absorption agent or a transvaginal absorption agent, a pulmonary absorption agent, an inhalant, an eye drop, a transdermal absorption agent, or an injection. In the therapeutic agent or prophylactic agent according to the present invention, the T-type calcium channel inhibitor according to the present invention may be used as a single therapeutic agent, or may be used as a mixture with other therapeutic agents. In administration, the T-type calcium channel inhibitor is generally administered as a pharmaceutical composition.

The therapeutic agent or prophylactic agent according to the present invention can be produced by a method commonly known by those skilled in the art using pharmacologically and pharmaceutically acceptable additives as necessary. For example, in the case of a tablet, a capsule or a granule, the therapeutic agent or prophylactic agent can be prepared using additives that are usually used, such as an excipient, a lubricant, a binder, a disintegrator, a wetting agent, a plasticizer and a coating agent. The oral liquid may be in the form of an aqueous or oily suspension, a solution, an emulsion, a syrup or an elixir, or may be provided as a dry syrup which is formulated into an oral liquid with water or any other suitable solvent before use. Such an oral liquid can be prepared using additives that are usually used, such as a suspending agent, a flavor, a diluent and an emulsifier.

The suppository can be prepared using additives such as an emulsifier, a suspending agent and a preservative as necessary with a suitable substance as a base, such as cocoa butter, laurin butter, macrogol, glycerogelatin, witepsol, sodium stearate or a mixture thereof. The injection can be prepared using a resolvent such as distilled water for injection, physiological saline, a 5% glucose solution or propylene glycol, and additives as necessary such as a solubilizer, a pH regulator, an isotonizing agent and a stabilizer.

When the T-type calcium channel inhibitor according to the present invention is administered to a human, the dose can be adjusted according to the age and conditions of a patient to which the inhibitor is administered. When the patient is an adult, normally the dose is generally about 0.1 to 1000 mg/person/day in the case of an oral agent or intrarectal administration, and generally about 0.05 mg to 500 mg/person/day in the case of an injection. These values are merely illustrative, and the dose of the agent is determined in accordance with conditions etc. of the patient.

The therapeutic agent or prophylactic agent for diseases according to the present invention, the effective action of which is a T-type calcium channel inhibitory action, is, for example, a therapeutic agent or prophylactic agent for neurogenic pains such as neuropathic pains. The therapeutic agent or prophylactic agent for diseases according to the present invention, the effective action of which is a T-type calcium channel inhibitory action, is not limited to the therapeutic agent or prophylactic agent for neurogenic pains. Other therapeutic agents or prophylactic agents for diseases according to the present invention, the effective action of which is a T-type calcium channel inhibitory action, include, for example, therapeutic agents or prophylactic agents for epilepsy, therapeutic agents or prophylactic agents for hyperaldosteronemia, therapeutic agents or prophylactic agents for inflammation, therapeutic agents or prophylactic agents for edemas, therapeutic agents or prophylactic agents for cardiac hypertrophy, therapeutic agents or prophylactic agents for heart failure, therapeutic agents or prophylactic agents for cardiomyopathy, therapeutic agents or prophylactic agents for atrial fibrillation, therapeutic agents or prophylactic agents for tachyarrhythmia, therapeutic agents or prophylactic agents for arteriosclerosis, therapeutic agents or prophylactic agents for nephritis, therapeutic agents or prophylactic agents for renal disorders and therapeutic agents or prophylactic agents for renal failure.

All the publications, patents and patent applications cited herein are incorporated herein by reference in their entirety.

EXAMPLES

The present invention will be described further in, detail by way of examples below, but the present invention is not limited to these examples. In examples, "%" is on a weight basis unless otherwise specified.

Preparation Example: Preparation of Compounds

The compounds described below were prepared or obtained in the following manner.

Sophoraflavanone G:

*Sophora* root (2 kg) was extracted with chloroform to obtain an extract. The obtained chloroform extract was subjected to silica gel column chromatography with a chloroform/methanol mixed liquid system and a hexane/acetone mixed liquid system, and a fraction containing an intended compound was detected by TLC analysis. Sophoraflavanone G was then isolated by performing preparative HPLC under the following conditions. HPLC: 600 Pump (Waters), 2489 UV/Visible Detector (Waters), column: YMC-Pack ODS-AM (250×20 mm i.d., YMC Co., Ltd.), guard column: YMC-Guardpack ODS-AM (50×20 mm i.d., YMC Co., Ltd.), mobile phase: liquid A; 0.1% acetic acid, liquid B; acetonitrile (0 min; liquid A: liquid B=20:80, 30 min; liquid A: liquid B=5:95), flow rate: 10.0 mL/min, detection wavelength: UV (280 nm), retention time (tR): 12 min.

DMSO (dimethyl sulfoxide) was used as a solvent for dissolving sophoraflavanone G.

6-Prenylnaringenin

6-Prenylnaringenin was purchased from Sigma-Aldrich Corporation (St. Louis, Mo.).

DMSO was used as a solvent for dissolving 6-prenylnaringenin.

8-Prenylnaringenin

8-Prenylnaringenin was purchased from Sigma-Aldrich Corporation (St. Louis, Mo.).

DMSO was used as a solvent for dissolving 8-prenylnaringenin.

Example 1: T-Type Calcium Channel Inhibitory Action of Sophoraflavanone G in Whole-Cell Patch Clamp Method A T-type calcium channel inhibitory action of sophoraflavanone G was measured by a whole-cell patch method using a human renal cell-derived cell line: EK 293 cell forced to express a human T-type calcium channel.

In the whole-cell patch method, a barium current passing as an inward current was measured in a potential jump from −80 mV to −20 mV with the holding potential set to −80 mV using, as an external solution and an internal solution, ones having the compositions shown below. Here, for eliminating influences of a high-threshold-activated-type calcium channel, a value obtained by subtracting from a peak current a current 150 ms after the start of stimulation was used as a T-current for data analysis.

External Solution Composition

Aqueous solution containing the following: 97 mM N-methyl-D-glucamine (NMDG);
10 mM $BaCl_2$;
10 mM 4-(2-hydroxyethyl)-1-piperazine ethanesulfonic acid (HEPES);

40 mM tetraethylammonium chloride (TEA-Cl); and
5 mM glucose
(pH 7.4).
Internal Solution Composition
Aqueous solution containing the following:
4 mM $MgCl_2$;
140 mM CsCl;
10 mM HEPES; and
5 mM glycol ether diamine tetraacetic acid (EGTA)
(pH 7.2).

Data obtained from the above-described experiment are shown in the table below.

TABLE 1

| Compound concentration (nM) | Inhibition rate (%) | Number of cases |
| --- | --- | --- |
| 500 | 25.9 | 4 |
| 1000 | 61.1 | 17 |
| 3000 | 97.7 | 6 |

Data obtained from the above-described experiment are shown in FIG. 1. In FIG. 1, the data are shown as a ratio (%) of a T-current at addition of a compound to a T-current at addition of a solvent (DMSO).

Example 2: T-Type Calcium Channel Inhibitory Action of 6-Prenylnaringenin in Whole-Cell Patch Clamp Method Except that sophoraflavanone G was replaced by 6-prenylnaringenin, the same procedure as in Example 1 was carried out to measure a T-type calcium channel inhibitory action of 6-prenylnaringenin.

Data obtained from the above-described experiment are shown in the table below.

TABLE 2

| Compound concentration (nM) | Inhibition rate (%) | Number of cases |
| --- | --- | --- |
| 300 | 0 | 6 |
| 1000 | 82.7 | 6 |
| 3000 | 99.0 | 6 |

Data obtained from the above-described experiment are shown in FIG. 2.

Example 3: T-Type Calcium Channel Inhibitory Action of 8-Prenylnaringenin in Whole-Cell Patch Clamp Method Except that sophoraflavanone G was replaced by 8-prenylnaringenin, the same procedure as in Example 1 was carried out to measure a T-type calcium channel inhibitory action of 6-prenylnaringenin.

Data obtained from the above-described experiment are shown in the table below.

TABLE 3

| Compound concentration (nM) | Inhibition rate (%) | Number of cases |
| --- | --- | --- |
| 300 | 16.4 | 8 |
| 1000 | 64.9 | 12 |

TABLE 3-continued

| Compound concentration (nM) | Inhibition rate (%) | Number of cases |
| --- | --- | --- |
| 3000 | 91.0 | 7 |
| 10000 | 99.9 | 6 |

Data obtained from the above-described experiment are shown in FIG. 3.

The IC50 values (nM) of the compounds in Examples 1 to 3 are shown in the table below. These 1050 values are values calculated by GraphPad Prism® (GraphPad Software, Inc.) using the results of Examples 1 to 3.

TABLE 4

| | IC50 (nM) |
| --- | --- |
| Sophoraflavanone G | 813.6 |
| 6-Prenylnaringenin | 800.9 |
| 8-Prenylnaringenin | 720.9 |

From the examples, it is apparent that the compounds used in the examples each have an excellent T-type calcium channel inhibitory action.

Example 4: Action of Sophoraflavanone G on NaHS-Induced Hyperalgesia

Into the paw sole of a male ddY mouse, 0.1 nmol/paw (volume: 10 μL/paw) of NaHS (sodium hydrogen sulfide) was administered alone, or 0.1 nmol/paw of NaHS and 1, 10 or 30 pmol/paw of sophoraflavanone G were administered in combination, and an action of sophoraflavanone G on NaHS-induced hyperalgesia was measured by an up-and-down method using a von Frey filament.

Here, NaHS (sodium hydrogen sulfide) is used as a $H_2S$ donor. $H_2S$ is a hyperalgesia-inducing substance which is involved in information transmission of pain through a $Ca_v3.2$ T-type calcium channel (see Kawabata A. et al. Hydrogen sulfide as a novel nociceptive messenger. Pain. 2007 November; 132(1-2): 74-81. Epub 2007 Mar. 7.).

Data obtained from the above-described experiment are shown in the table below.

TABLE 5

| Treatment | Hyperalgesia threshold (g) Average value ± standard error | Number of cases |
| --- | --- | --- |
| Solvent + solvent | 0.43 ± 0.07 | 6 |
| NaHS (0.1 nmol/paw sole) + solvent | 0.06 ± 0.01 | 6 |
| NaHS (0.1 nmol/paw sole) + sophoraflavanone G (1 pmol/paw sole) | 0.11 ± 0.04 | 4 |
| NaHS (0.1 nmol/paw sole) + sophoraflavanone G (10 pmol/paw sole) | 0.35 ± 0.07 | 4 |
| NaHS (0.1 nmol/paw sole) + sophoraflavanone G (30 pmol/paw sole) | 0.34 ± 0.10 | 4 |

Data obtained from the above-described experiment are shown in FIG. 4. As shown in the above table and FIG. 4, it is apparent that sophoraflavanone G inhibits NaHS-induced hyperalgesia, and thus exhibits a T-type calcium channel inhibitory action.

Example 5: Action of 6-Prenylnaringenin on NaHS-Induced Hyperalgesia

Except that 6-prenylnaringenin was used in place of sophoraflavanone G, the same procedure as in Example 4 was carried out to measure an action of 6-prenylnaringenin on NaHS-induced hyperalgesia. The obtained data are shown in the table below.

TABLE 6

| Treatment | Hyperalgesia threshold (g) Average value ± standard error | Number of cases |
|---|---|---|
| Solvent + solvent | 0.62 ± 0.00 | 4 |
| NaHS (0.1 nmol/paw sole) + solvent | 0.21 ± 0.04 | 4 |
| NaHS (0.1 nmol/paw sole) + 6-prenylnaringenin (0.1 nmol/paw sole) | 0.28 ± 0.07 | 4 |
| NaHS (0.1 nmol/paw sole) + 6-prenylnaringenin (1 nmol/paw sole) | 0.31 ± 0.06 | 4 |
| NaHS (0.1 nmol/paw sole) + 6-prenylnaringenin (10 nmol/paw sole) | 0.52 ± 0.09 | 4 |

Data obtained from the above-described experiment are shown in FIG. 5. As shown in the above table and FIG. 5, it is apparent that 6-prenylnaringenin inhibits NaHS-induced hyperalgesia, and thus exhibits a T-type calcium channel inhibitory action.

Example 6: Action of 8-Prenylnaringenin on NaHS-Induced Hyperalgesia

Except that 8-prenylnaringenin was used in place of sophoraflavanone G, the same procedure as in Example 4 was carried out to measure an action of 8-prenylnaringenin on NaHS-induced hyperalgesia. The obtained data are shown in the table below.

TABLE 7

| Treatment | Hyperalgesia threshold (g) Average value ± standard error | Number of cases |
|---|---|---|
| Solvent + solvent | 0.60 ± 0.07 | 9 |
| NaHS (0.1 nmol/paw sole) + solvent | 0.21 ± 0.02 | 9 |
| NaHS (0.1 nmol/paw sole) + 8-prenylnaringenin (0.1 nmol/paw sole) | 0.23 ± 0.04 | 4 |
| NaHS (0.1 nmol/paw sole) + 8-prenylnaringenin (1 nmol/paw sole) | 0.41 ± 0.04 | 9 |
| NaHS (0.1 nmol/paw sole) + 8-prenylnaringenin (10 nmol/paw sole) | 0.55 ± 0.05 | 8 |

Data obtained from the above-described experiment are shown in FIG. 6. As shown in the above table and FIG. 6, it is apparent that 8-prenylnaringenin inhibits NaHS-induced hyperalgesia, and thus exhibits a T-type calcium channel inhibitory action.

Example 7: Action of Sophoraflavanone G on L-Type $Ca^{2+}$ Channel

1. Experimental Animals

For the experiment, 7 to 10 week-old male Wistar rats (Japan SLC, Inc., Shizuoka, Japan) were used. These experimental animals were bred in a chamber with a 12-hour light-dark cycle maintained at a temperature of about 24° C. while they were allowed to freely take tap water and a solid feed (Oriental Yeast Co., Ltd., Tokyo, Japan).

2. Preparation of Specimen

The rats were caused to hemorrhage to death by cutting the carotid artery under anesthesia, and the thoracic aorta was extracted. Connective tissues and fat were removed from the thoracic aorta in a cooled modified Kreb's liquid. A 1 mm-wide ring preparation was prepared from the thoracic aorta, and the lumen of the specimen was rubbed with rubber to remove the endothelium. Removal of the endothelium was confirmed by the fact that a relaxation response did not occur when acetylcholine (Ach) was made to act on the specimen caused to pre-contract by phenylephrine (Phe).

3. Measurement of Tension

Two 100 μm tungsten wires were inserted into the lumen of the 1 mm-wide ring preparation, and the ring preparation was transferred to a liquid bath with a volume of 10 mL. The liquid bath had a double-glass structure, and warm water heated to 37° C. in a thermostatic bath was circulated to the outer layer of the liquid bath to maintain experimental conditions of a fixed temperature. The other ends of tungsten wires inserted into the lumen of the ring preparation were fixed to a tension transducer, and a change in tension of the specimen was isometrically measured. Signals from the tension transducer passed through a blood pressure amplifier to be recorded by a pen recorder. An initial stretching tension of 1 g was applied in a normal Kreb's liquid, and the specimen was equilibrated for 1 hour, and then caused to contract once by a $10^{-6}$ M phenylephrine solution. This procedure was necessary for obtaining stable results. At the end of the experiment, verapamil (Vera) ($10^{-5}$ M) and papaverine ($10^{-4}$ M) were added to completely relax the specimen. The level at this time was set to 0 for all the measurements of a change in tension.

4. Reagents

The reagents used were as follows.

Normal Kreb's liquid: NaCl (118 mM), KCl (4.7 mM), $CaCl_2$ (2.5 mM), $MgCl_2$ (1.2 mM), $NaHCO_3$ (25 mM), $KH_2PO_4$ (1.2 mM) and glucose (10 mM) were diluted with $H_2O$ to 1 L, and ventilated for 10 minutes with a mixed gas of 95% of $O_2$ and 5% of $CO_2$, and 2.5 mL of a 1 M $CaCl_2$ solution was then added.

Kreb's liquid (K50): NaCl (73.9 mM), KCl (48.8 mM), $CaCl_2$ (2.5 mM), $MgCl_2$ (1.2 mM), $NaHCO_3$ (25 mM), $KH_2PO_4$ (1.2 mM) and glucose (10 mM) were diluted with $H_2O$ to 1 L, and ventilated for 10 minutes with a mixed gas of 95% of $O_2$ and 5% of $CO_2$, and 2.5 mL of a 1 M $CaCl_2$ solution was then added.

Acetylcholine hydrochloride (Ach, manufactured by Sigma)

Verapamil hydrochloride (Vera, manufactured by Eisai Co., Ltd. (Tokyo))

Papaverine hydrochloride (manufactured by Sigma)

5. Results

A contraction experiment using a rat aortic smooth muscle specimen freed of the vascular endothelium was conducted to examine effects of sophoraflavanone G, which had exhibited a T-type calcium channel inhibitory effect, on an L-type $Ca^{2+}$ channel. Complete removal of the endothelium was confirmed by the fact that relaxation did not occur when $10^{-6}$ M acetylcholine was made to act on the specimen caused to contract by $10^{-6}$ M phenylephrine.

Thereafter, the specimen was washed three times with the Normal Kreb's liquid, and to the specimen caused to pre-contract by the Kreb's liquid (K50) containing 50 mM potassium ions, 1 μL of 1 μM of sophoraflavanone G (final concentration: 0.001 μM) dissolved in DMSO, 2 μL of 1 μM of the sophoraflavanone G (final concentration: 0.003 μM), 7 μL of 1 μM of the sophoraflavanone G (final concentration: 0.01 μM), 2 μL of 10 μM of the sophoraflavanone G (final concentration: 0.03 μM), 7 μL of 10 μM of the sophoraflavanone G (final concentration: 0.1 µM), 2 µL of 10 µM of the sophoraflavanone G (final concentration: 0.3 µM), 7 µL of 100 µM of the sophoraflavanone G (final concentration: 1 µM) and 2 µL of 1000 µM of the sophoraflavanone G (final concentration: 3 µM) were accumulatively added in a liquid bath containing 10 mL of the Kreb's liquid. A contraction experiment using a rat aortic smooth muscle specimen freed of the vascular endothelium was conducted to examine effects of sophoraflavanone G, which had exhibited a T-type calcium channel inhibitory effect, on an L-type $Ca^{2+}$ channel. Inhibitory rates (%) on contraction by K50 are shown in the table below, and a measurement chart is shown in FIG. 8.

TABLE 8

| Sophoraflavanone G (µM) | | | | | | | |
|---|---|---|---|---|---|---|---|
| 0.001 | 0.003 | 0.01 | 0.03 | 0.1 | 0.3 | 1 | 3 |
| Inhibitory rate (%) 0.0 | 0.0 | 5.6 | 5.6 | 5.6 | 5.6 | 11.1 | 8.3 |

The results of measurement of effects of DMSO, which was used as a solvent for dissolving sophoraflavanone G, on an L-type $Ca^{2+}$ channel are shown in the table below and FIG. 7.

TABLE 9

| DMSO (%) | | | | | | | |
|---|---|---|---|---|---|---|---|
| 0.1 | 0.3 | 1 | 1.3 | 2 | 2.3 | 3 | 3.3 |
| Inhibitory rate (%) 0.0 | 0.0 | 0.0 | 0.0 | 0.0 | 0.0 | 5.6 | 2.2 |

As shown in the above table and FIG. 8, sophoraflavanone G did not relax the specimen caused to pre-contract by K50. From this measurement result, it has been confirmed that sophoraflavanone G does not act on an L-type calcium channel.

Example 8: Action of 6-Prenylnaringenin on L-Type $Ca^{2+}$ Channel

Except that 6-prenylnaringenin was used in place of sophoraflavanone G, the same procedure as in Example 7 was carried out to examine effects on an L-type $Ca^{2+}$ channel. Inhibitory rates (%) on contraction by K50 are shown in the table below, and a measurement chart is shown in FIG. 9.

TABLE 10

| 6-Prenylnaringenin (µM) | | | | | | | |
|---|---|---|---|---|---|---|---|
| 0.001 | 0.003 | 0.01 | 0.03 | 0.1 | 0.3 | 1 | 3 |
| Inhibitory rate (%) 0.0 | 0.0 | 4.1 | 6.1 | 4.1 | 4.1 | 4.1 | 4.1 |

As shown in the above table and FIG. 9, 6-prenylnaringenin did not relax the specimen caused to pre-contract by K50. From this measurement result, it has been confirmed that 6-prenylnaringenin does not act on an L-type calcium channel.

Example 9: Action of 8-Prenylnaringenin on L-Type $Ca^{2+}$ Channel

Except that 8-prenylnaringenin was used in place of sophoraflavanone G, the same procedure as in Example 7 was carried out to examine effects on an L-type $Ca^{2+}$ channel. Inhibitory rates (%) on contraction by K50 are shown in the table below, and a measurement chart is shown in FIG. 10.

TABLE 11

| 8-Prenylnaringenin (µM) | | | | | | | |
|---|---|---|---|---|---|---|---|
| 0.001 | 0.003 | 0.01 | 0.03 | 0.1 | 0.3 | 1 | 3 |
| Inhibitory rate (%) 0.0 | 0.0 | 7.4 | 0.0 | 11.1 | 14.8 | 22.2 | 25.9 |

As shown in the above table and FIG. 10, 8-prenylnaringenin did not relax the specimen caused to pre-contract by K50. From this measurement result, it has been confirmed that 8-prenylnaringenin does not act on an L-type calcium channel.

From these experiments, it has been confirmed that none of sophoraflavanone G, 6-prenylnaringenin and 8-prenylnaringenin acts on an L-type calcium channel. That is, sophoraflavanone G, 6-prenylnaringenin and 8-prenylnaringenin have been each confirmed to be a T-type calcium channel-specific inhibitor (T-type calcium channel-selective inhibitor) which does not act on an L-type calcium channel while acting on a T-type calcium channel.

The T-type calcium channel-specific (selective) inhibitor does not have actions caused by an L-type calcium channel inhibitor, such as a myocardial contraction inhibitory action and a vascular smooth muscle relaxing action, and thus can be used as a safer therapeutic agent (e.g. neurogenic pain therapeutic agent). More specifically, the T-type calcium channel-specific inhibitor does not have a myocardial contraction inhibitory action and a vascular smooth muscle relaxing action, and therefore has the advantage that a decrease in cardiac output and dilation of blood vessels are hard to occur, so that side effects resulting from disorders of cardiovascular systems, such as a decrease in blood pressure, postural hypotension or edemas can be reduced.

Formulation Example 1

A granule containing the T-type calcium channel inhibitor according to the present invention was produced in accordance with the following procedure.

TABLE 12

| 6-Prenylnaringenin | 10 mg |
|---|---|
| Lactose | 700 mg |
| Corn starch | 274 mg |
| HPC-L | 16 mg |
| Total | 1000 mg |

6-Prenylnaringenin and lactose were put through a 60-mesh screen, and corn starch was put through a 120-mesh screen. They were mixed by a V-type mixer. To the mixed powder was added an aqueous solution of low-viscosity hydroxypropyl cellulose (HPC-L), and the mixture was kneaded. The obtained product was granulated (extrusion granulation, pore diameter: 0.5 to 1 mm), and then dried. The obtained dry grains were sieved by a vibrating screen (12/60 mesh) to obtain a granule.

Formulation Example 2

An intravenous preparation containing the T-type calcium channel inhibitor according to the present invention was produced in accordance with the following procedure.

TABLE 13

| 6-Prenylnaringenin | 100 mg |
| Saturated fatty acid glyceride | 1000 ml |

The solution of the components is normally intravenously administered to a patient at a rate of 1 ml per minute.

INDUSTRIAL APPLICABILITY

The T-type calcium channel inhibitor according to the present invention which is a flavanone compound has an excellent T-type calcium channel inhibitory action. The T-type calcium channel inhibitor according to the present invention is very useful in the fields of, for example, medical cares, pharmaceutical products and prophylactic agents.

The invention claimed is:

1. A method for the treatment of neuropathic pain, comprising:
administering to a patient in need of such treatment an effective amount of a T-type calcium channel inhibitor selected from the group consisting of (2S)-5,7-dihydroxy-2,3-dihydro-2-(2,4-dihydroxyphenyl)-8-[(R)-5-methyl-2-(1-methylethenyl)-4-hexenyl]-4H-1-benzopyran-4-one, (2S)-5,7-dihydroxy-2,3-dihydro-2-(2,4-dihydroxyphenyl)-6-[(R)-5-methyl-2-(1-methylethenyl)-4-hexenyl]-4H-1-benzopyran-4-one, (2S)-5,7-dihydroxy-2,3-dihydro-2-(4-hydroxyphenyl)-6-(3-methyl-2-butenyl)-4H-1-benzopyran-4-one, and (2S)-5,7-dihydroxy-2-(3-hydoxy-4-methoxyphenyl)-2,3-dihydro-4H-chromen-4-one, a pharmaceutically acceptable salt of any of these compounds, and a solvate of any of these compounds.

* * * * *